Figure 1:
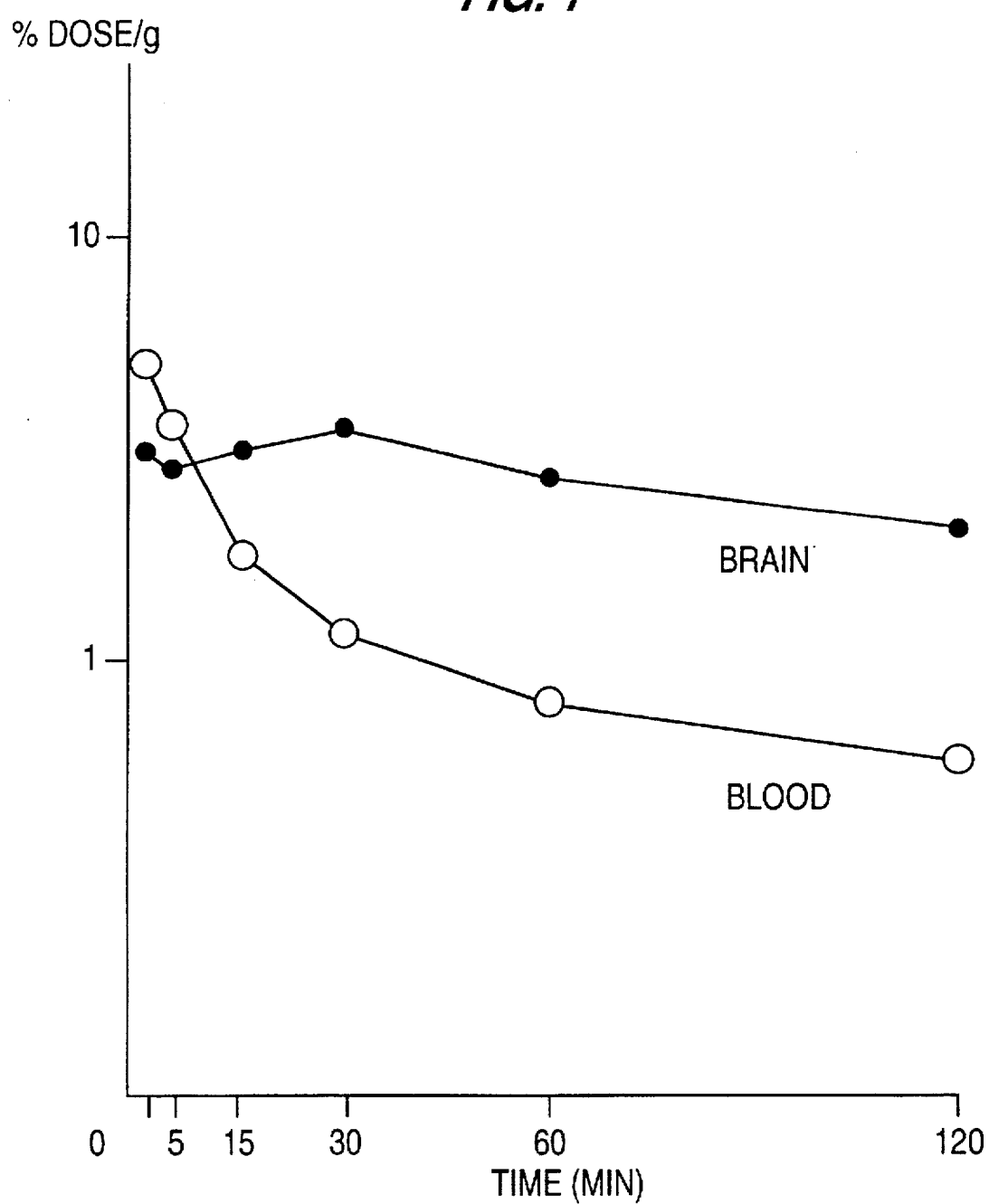

United States Patent [19]

Yokoyama et al.

[11] Patent Number: 5,739,117
[45] Date of Patent: Apr. 14, 1998

[54] AGENT FOR IMPROVING CEREBRAL METABOLISM INCLUDING GLUCOSE ESTER DERIVATIVES

[75] Inventors: Akira Yokoyama, Otu; Fumio Yoneda, Matsubara, both of Japan

[73] Assignee: Fujimoto Pharmaceutical Co., Ltd., Osaka, Japan

[21] Appl. No.: 446,587

[22] PCT Filed: Oct. 17, 1994

[86] PCT No.: PCT/JP94/01741

§ 371 Date: Jul. 19, 1995

§ 102(e) Date: Jul. 19, 1995

[87] PCT Pub. No.: WO95/11031

PCT Pub. Date: Apr. 27, 1995

[30] Foreign Application Priority Data

Oct. 22, 1993 [JP] Japan ............................ 5-298870

[51] Int. Cl.$^6$ .................................................. A61K 31/70
[52] U.S. Cl. ................................................ 514/25
[58] Field of Search ............................... 536/4.1; 514/25

[56] References Cited

U.S. PATENT DOCUMENTS 5,374,716  12/1994  Biermann et al. .............. 536/18.6

*Primary Examiner*—Elli Peselev
*Attorney, Agent, or Firm*—Wenderoth, Lind & Ponack

[57] ABSTRACT

An agent for improvement of cerebral metabolism, containing as active ingredient a glucose ester derivative presented by the formula:

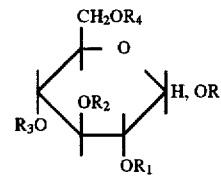

and wherein the anomeric substitute in the formula is either α or β; R to $R_4$, each represents H atom, a straight or branched acyl or a ring containing acyl having 2 to 8 carbon atoms, provided that at least one of said R to $R_4$ is the acyl group.

The present agent is effective for the treatment of cerebral disorders resulting from hypoglycemic shock, the reduced capacity of active glucose trasport through the blood-brain barrier, and senile dementia or senile movement functional disorders.

3 Claims, 5 Drawing Sheets

AGENT FOR IMPROVING CEREBRAL METABOLISM INCLUDING GLUCOSE ESTER DERIVATIVES

TECHNOLOGICAL ASPECT

This invention provides an agent for improving cerebral metabolism, including glucose ester derivatives (glucose pyranose derivatives), which is excellent in penetrating activity across the blood-brain barrier.

BACKGROUND

Transport from blood to the cerebral tissue of substances necessary for the maintenance of cerebral function is extremely impeded by the blood-brain barrier. Glucose, which is a sole and very important energy source for the cerebral tissue, is therefore, no exception as reported by Goldstein (*Scientific America.*, 254:74–83, 1986). The supply of glucose from blood to inside of brain is controlled by carrier proteins which are specific for the blood-brain barrier, through their selective and active transport from the outside of the barrier to the cerebral tissue. Glucose transported to the cerebral tissue, is metabolized by hexokinase to glucose-6-phosphate, which is a very important intermediate in glucose catabolism system, and then entered into a metabolic pathway where it is degraded up to an end product of the energy generating system while generating simultaneously with high energy-phosphoric compounds such as ATP through its linked phosphorylation reaction under influence of oxidation, decarboxylation and other reactions.

Approximately 20% of the total oxygen consumption in the body takes place in the brain where a large amount of glucose is concomitantly consumed. In the cerebral tissue, however, there is no sugar storage in the form of glycogen, and therefore, the brain is liable to fall into a state of energy metabolism dysfunction within a short time when glucose supply is disturbed due to blood hypoglycemia or to a decrease in the capacity of the blood-brain barrier transport, the conditions of which are just similar to those of respiratory or circulation disorders.

In an acute situation, disorders appear first in an metabolically active tissue site with the highest sugar consumption, then to the next site in an order of sugar consumption degrees. A cerebrum dysfunction starts at a blood sugar level lower than 60 mg/dl, and hypoglycemic coma may be caused when its level becomes lower than 20 mg/dl. In this case, 50% of human subjects will die unless they get an improvement in the cerebral energy metabolic disorder within 5 minutes. Even if survived, they may suffer from sequela such as dementia and a vegetable state depend on the degree of disorder. Similar to brain hypoxia, an irreversible neuronal symptom is known to progress in some cases even afer revival from coma as a result of regressive degeneration due to delayed cell death following excess release of glutamic acid and elicitation of a calcium concentration increase in neuronal cells, particularly when the coma state prolonged or spasm occurred repeatedly.

The current treatment that has been considered best for cerebral disorders resulting from hypoglycemic shock and disturbance in consciousness associated with diabetic hypoglycemia is oral or intravenous administration of glucose. This therapy method has been widely exercised. This treatment can raise a blood sugar level immediately. However, since glucose per se cannot cross the barrier, glucose needs to be captured first by carrier proteins and then subjected to an active and selective transport together with its carrier through the blood-brain barrier into cerebral tissues. Because of this fact, a time-lag of a few minutes is inevitable between administration of glucose and attainment of a sufficient concentration of glucose at a site of the cerebral tissue. This detriment in glucose administration has remained to be solved, since supply of energy source at a sufficient level to the cerebral tissue of these patients must be carried out as urgently as possible.

In the same token as above, a decreased capacity in the active transport of glucose at the blood-brain barrier due to aging or cerebral disorders can result in reducing cerebral metabolic functional competence and causing necrosis of the cerebral tissue. Thereby, the administration of glucose, as mentioned above, to the patients with incompetence in active transport of glucose through the blood-brain barrier would result in only an increase in blood sugar levels, but hardly in providing their cerebral tissue with energy source. Thus, this therapy cannot be an efficient one for improvement or maintenance of cerebral metabolism in these patients.

In ventors of this invention studied this problem with use of 1, 3, 4, 6-tetra-O-acetyl-N-(m-iodobenzoyl)-glucosamine and 1, 3, 4, 6-tetra-O-pivaloyl-N-(m-iodobenzoyl)-glucosamine, and reported a high transport rate of glucosamine ester derivatives across the blood-brain barrier in *Journal of Labelled Compounds and Radiopharmaceuticals*, 30:300–303, 1991. However, anticipated has been the appearance of glucose derivatives such as those that have a high transport rate at the blood-brain barrier, regardless of the active transport regulatory condition, and can reach the cerebral tissues quickly so as to be converted to glucose-6-phosphate, therefore act very effectively in improvement of the cerebral metabolism in the patients who suffered blood hypoglycemic shock or diabetic hypoglycemic coma. Thus, this invention is intended to explore this type of contemplation.

DISCLOSURE OF THE INVENTION

These inventors gave rise to the discoveries described below, leading to the invention presented herein. The discoveries are as follws: 1) glucose ester derivatives, having a transport mechanism different from that for glucose, can reach the cerebral tissue after crossing the blood-brain barrier without any substantial time lag that often occurs in case of glucose transport; 2) in the cerebral tissues, glucose ester derivatives can be converted to the aforementioned catabolic intermediate metabolite, glucose-6-phosphate, at much more accelerated rate than the catabolic rate of these derivatives present in somatic tissues outside the blood-brain barrier. These findings led us to this invention described herein. That is, in this invention, a glucose ester derivative of the formula below.

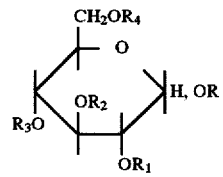

(1)

[The anormeric substitute in the formula is either α or β; $R-R_4$, are identical or different each other, and each represents H atom, a straight or branched acyl group having 2 to 8 carbons, or acyl group containing a ring structure, and in addition, at least 1 of said $R-R_4$ is the acyl group is used as an active ingredient of the present cerebral metabolism improving agent.]

THE BEST MODES FOR THE PRACTICE OF THE INVENTION

Any of the glucose ester derivatives, shown as the general formula above, can be converted quickly into glucose-6- phosphate following administration. Because of this characteristic, these derivatives are most effective in improvement of cerebral metabolism in such patients who suffered from blood hypoglycemic shock, and diabetic hypoglycemic coma that require urgently the supply of glucose energy source, and also in the patients who suffer from dementia or motor function disorder resulted from lack of glucose energy source due to the transport disfunction at the blood-brain barrier.

The most preferable glucose ester derivatives in this invention are as follows: 1, 3, 4, 6,-tetra-O-acetyl-D-glucose; 1, 2, 3, 4, 6,-penta-O-acetyl-D-glucose; 1, 2-di-O-acetyl-3, 4, 6-tri-O-(2-methylbutyryl)-D-glucose; 1, 3,-di-O-acetyl-6-O-butyryl-D-glucose; 1, 3, 4,-tri-O-acetyl-6-O-nicotinoyl-D-glucose; 1, 2-di-O-benzoyl-D-glucose; 1-O-cinnamoyl-D-glucose, etc. In particular, 1, 2-di-O-acetyl-D-glucose, 3, 4, 6-tri-O-acetyl-D-glucose, 1, 3, 4, 6-tetra-O-acetyl-D-glucose, 1, 2, 3, 4, 6-penta-O-acetyl-D-glucose are very effective and preferred.

Glucose ester derivatives of this invention can be administered orally or non-orally in formulas of tablets, capsules, granules, syrup, troche, elixir, injection, and suspension that are manufactured in general pharmacological preparation methods with use of fillers, disintegrant, binders, lubricants, sweetening agents, alcohol, solubilizer, buffering agents, water-soluble bases, emulsifying agents, suspending agents.

The effects of the invention shall be minutely stated in connection with the following Reference Examples and Examples, and however, these should not be taken as being limitative to the present invention and the working effects thereof.

[REFERENCE EXAMPLE 1]

The compound, 1, 3, 4, 6-tetra-O-acetyl-2-$^{18}$F-D-glucose ($^{18}$F-AFDE) labelled with an electrophilic reagent, $^{18}$F, was prepared according to the method of Shiue et al (*Journal of Nuclear Medicine*, 23:889–903, 1982); $^{18}$F acetate, obtained by passing 18.2 mg $^{18}$F through a column filled with sodium acetate, was subjected to the reaction at 0° C. with 3, 4, 6-tri-O-acetyl-glucal in solvent of freon-11, resulting in a yield of 60 mg $^{18}$F-AFDG.

[REFERENCE EXAMPLE 2]

The control compound, 2-$^{18}$F-D-glucose ($^{18}$F-FDG) was obtained in an amount of 10 mg by addition of 5 ml of 1N solution of hydrochloric acid to 30 mg of $^{18}$F-AFDG of the above Reference Example 1 followed by heating the mixture at 130° C. for 15 minutes.

[EXAMPLE 1]

Normal male mice of the ddy strain at 6 weeks of age were injected intravenously through tail vein with 0.05 ml of mM $^{18}$F in DMSO solution. Measurement of its blood concentrations and radioactivities in the cerebral tissue of the mice revealed that the radioactivity could be detected in the cerebral tissue immediately after administration, and levels of the radioactivity increased up to 30 minutes, whereas the blood radioactivity levels decreased consistently following administration, and at 10 minutes of administration, and thereafter the radioactivity was found to be higher in the cerebral tissue than in the blood (FIG. 1).

[EXAMPLE 2]

Figure 2:
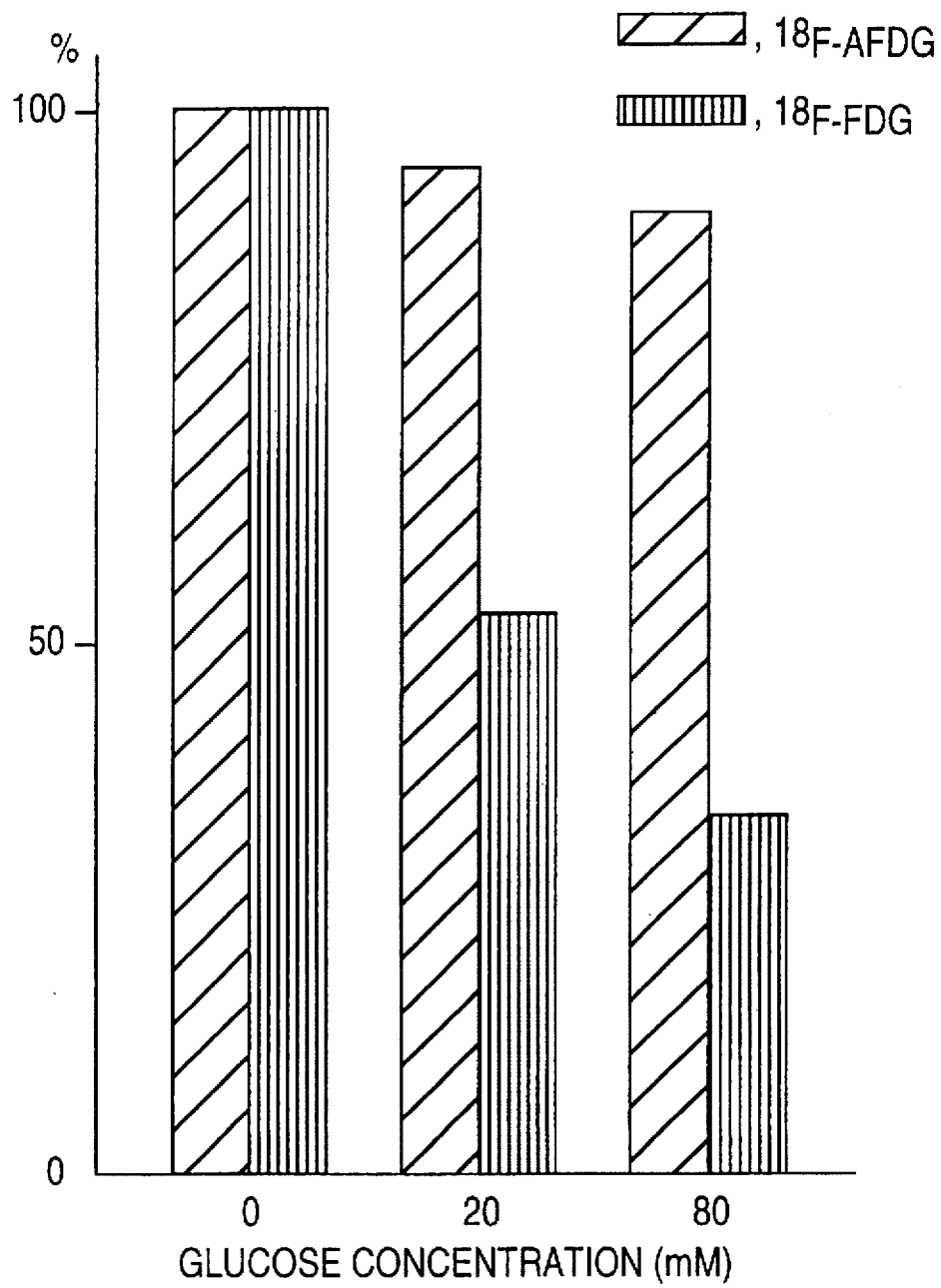

Two tenth ml of $^{18}$F-FDG or $^{18}$F-AFDG in 50% DMSO solution was injected into the carotid artery of three different groups of rats: the first group of rats injected without addition of glucose; the second group with 20 mM glucose; the third group with 80 mM glucose, and then the radioactivity of the respective labelled compound transported into the cerebral tissue was measured. The transport rate of $^{18}$F-FDG to the cerebral tissue was decreased inversely as the concentration of glucose was increased. On the other hand, $^{18}$F-FDG, an ester derivative, could reach the cerebral tissue at transport rates higher than 90% with no competition even to the maximum concentration of glucose, 80 mM (FIG. 2). The finding that the transport of the glucose ester derivative to the cerebral tissue was not influenced by varying concentratioins of glucose indicates that there is a transport mechanism across the blood-brain barrier for the glucose ester derivative different from the mechanism for glucose transport.

[EXAMPLE 3]

Mice were given an intravenous injection of 0.05 ml solution of 0.5 mM $^{18}$F-AFD in DMSO. The cerebral tissue harvested at 0.5, 2, 5, 60 and 180 minutes were homogenized for one minute in ethanol, and then centrifuged at 700×g for 10 minutes. The supernatant was collected for individual measurements of $^{18}$F-AFDG, its intra-cerebral metabolites, $^{18}$F-FD and $^{18}$F-FDG-6-phosphate.

Figure 3:
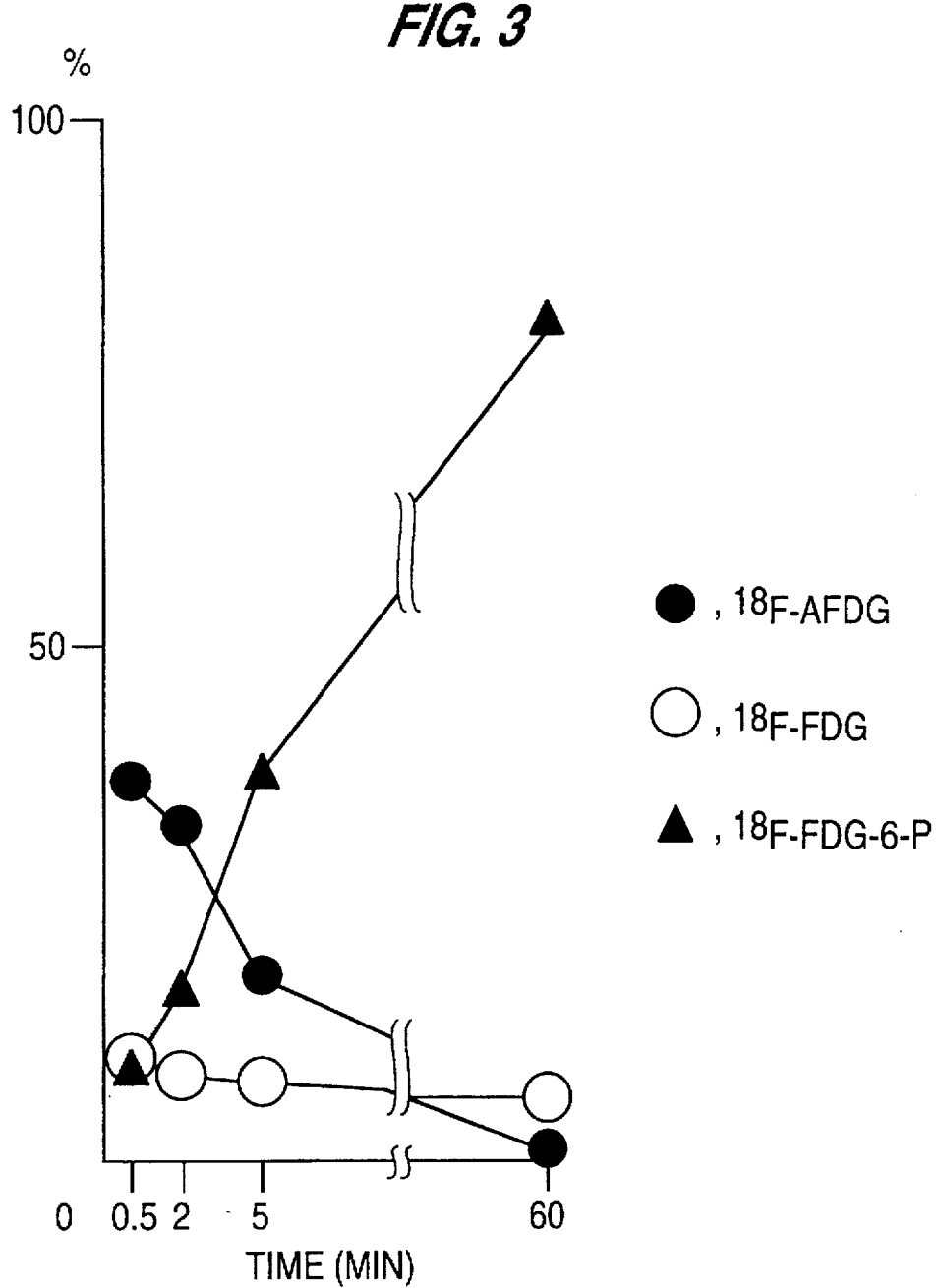

It was noted that approximately 40% $^{18}$F-AFDG of reached the cerebral tissue, and also its intra-cerebral metaboletes, $^{18}$F-FD and $^{18}$F-FDG-6-phosphate emerged within 0.5 minute following administration. Thereafter, $^{18}$F-AFDG was metabolized into $^{18}$F-FDG-6-phosphate, and the concentration of the latter was raised markedly (FIG. 3).

Figure 4:
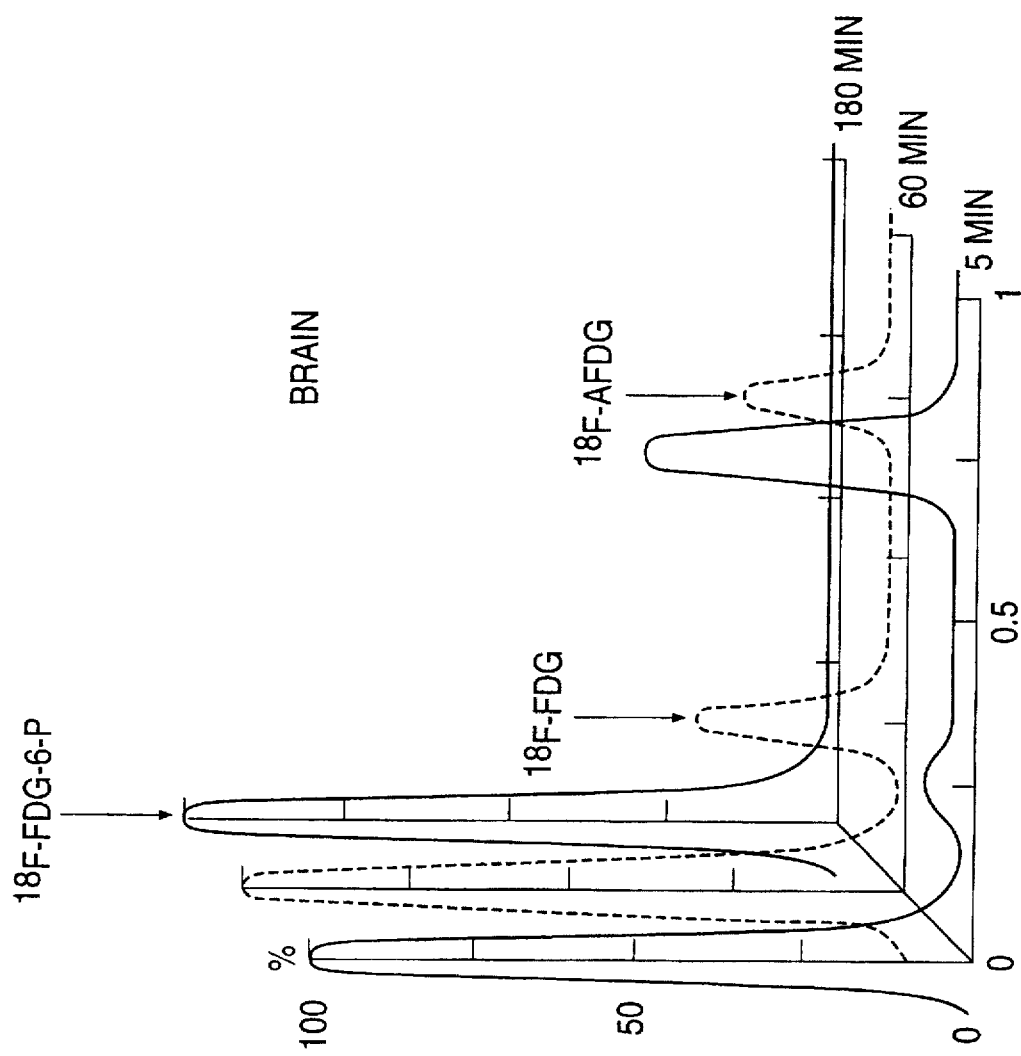
Figure 5:
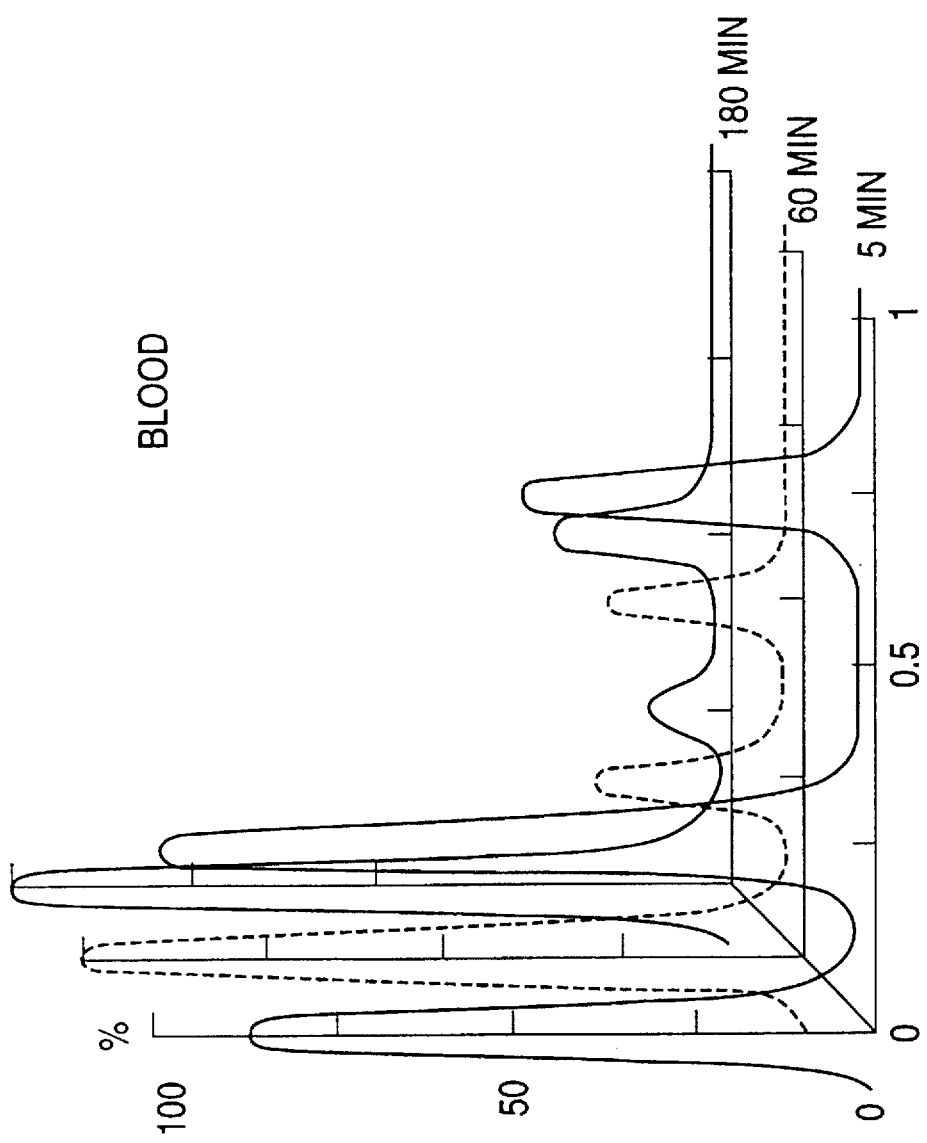

When intra-cerebral concentrations of metabolites were compared with those in the blood at 5, 60 and 180 minutes following administration of $^{18}$F-AFDG, $^{18}$F-FDG-6-phosphate was found at the highest proportion in the cerebral tissue at the respective time points of measurement, and at 180 minutes the entire $^{18}$F-AFDG was found to be metabolized into $^{18}$F-FDG-6-phosphate, demonstrating a very rapid metabolic rate of the glucose ester derivative to glucose-6-phosphate, especially in the cerebral tissue (FIGS. 4 and 5).

In FIGS. 4 and 5, peaks at 0, 0.25, and 0.75 on axis represent peaks of $^{18}$F-FDG-6-phosphate, $^{18}$F-FDG and $^{18}$F-AFDG, respectively, where the highest peak measured is designated 100%, and other two peaks are expressed as relative ratios of the highest.

LEGEND OF DRAWINGS

[FIG. 1]

Kinetic changes in radioactivities in the blood and the cerebral tissue of the mice injected with $^{18}$F-AFDG.

[FIG. 2]

Transport rates to the cerebral tissue of $^{18}$F-AFDG and $^{18}$F-FDG administered to rats with varying concentrations of glucose.

[FIG. 3]

Kinetic changes of $^{18}$F-AFDG, and its metabolites in the cerebral tissue of the mice administered with this labelled compound.

[FIG. 4]

Kinetic changes in the ratio of intra-cerebral concentrations of $^{18}$F-AFDG and its metabolites in the mice administered this labelled compound.

[FIG. 5]

Kinetic changes in the ratio of blood concentrations of $^{18}$F-AFDG and its metabolites in mice administered this labelled compound.

We claim:

1. A method for the treatment of cerebral functional disorders resulting from a reduced capacity for active glucose transport through a blood-brain barrier in a patient, which comprises administering to said patient an effective amount of an agent containing as an effective component a glucose ester derivative represented by the formula:

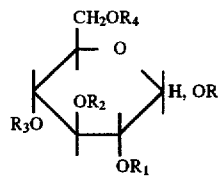

in which the anomeric form is either α or β; each of $R$–$R_4$ is selected from the group consisting of H atom, a straight or branched acyl group having 2 to 8 carbon atoms, and a ring containing acyl group, provided that at least one of the said $R$–$R_4$ is the acyl group and a pharmaceutically acceptable carrier.

2. The method according to claim 1, wherein said effective component is selected from the group consisting of 1,3,4,6-tetra-O-acetyl-D-glucose; 1,2,3,4,6-penta-O-acetyl-D-glucose; 1,2-di-O-acetyl-3,4,6-tri-O-(2-methylbutyryl)-D-glucose; 1,3,-di-O-acetyl-6-O-butyryl-D-glucose; 1,3,4-tri-O-acetyl-6-O-nicotinoyl-D-glucose; 1,2-di-O-benzoyl-D-glucose; 1-O-cinnamoyl-D-glucose; 1,2-di-O-acetyl-D-glucose and 3,4,6-tri-O-acetyl-D-glucose.

3. The method according to claim 2, wherein the effective component is 1,3,4,6-tetra-O-acetyl-D-glucose.

* * * * *